(12) United States Patent  
Lee

(10) Patent No.: US 9,151,841 B2  
(45) Date of Patent: Oct. 6, 2015

(54) PROVIDING AN ULTRASOUND SPATIAL COMPOUND IMAGE BASED ON CENTER LINES OF ULTRASOUND IMAGES IN AN ULTRASOUND SYSTEM

(75) Inventor: Kwang Ju Lee, Seoul (KR)

(73) Assignee: SAMSUNG MEDISON CO., LTD., Hongchun-Gun, Kangwon-Do (KR)

( * ) Notice: Subject to any disclaimer, the term of this patent is extended or adjusted under 35 U.S.C. 154(b) by 93 days.

(21) Appl. No.: 13/221,330

(22) Filed: Aug. 30, 2011

(65) Prior Publication Data

US 2012/0095342 A1     Apr. 19, 2012

(30) Foreign Application Priority Data

Oct. 19, 2010     (KR) .................. 10-2010-0101608

(51) Int. Cl.  
*A61B 8/00*     (2006.01)  
*G01S 15/89*    (2006.01)  
*A61B 8/08*     (2006.01)  
*G01S 7/52*     (2006.01)

(52) U.S. Cl.  
CPC ........... *G01S 15/8995* (2013.01); *A61B 8/5253* (2013.01); *G01S 7/52085* (2013.01)

(58) Field of Classification Search  
CPC .................. G01S 15/8995; G01S 7/52085  
USPC ....................................... 600/447  
See application file for complete search history.

(56) References Cited

U.S. PATENT DOCUMENTS

| | | | |
|---|---|---|---|
| 5,257,624 A * | 11/1993 | Fraser et al. | 600/437 |
| 5,921,932 A * | 7/1999 | Wright et al. | 600/447 |
| 6,390,981 B1 | 5/2002 | Jago | |
| 6,790,181 B2 | 9/2004 | Cai et al. | |

(Continued)

FOREIGN PATENT DOCUMENTS

| EP | 1 903 353 A1 | 3/2008 |
|---|---|---|
| EP | 1898233 A1 | 3/2008 |

(Continued)

OTHER PUBLICATIONS

Korean Office Action, issued in Korean Patent Application No. 10-2010-0101608, dated Dec. 27, 2011.

(Continued)

*Primary Examiner* — Jonathan Cwern  
*Assistant Examiner* — Amelie R Gillman  
(74) *Attorney, Agent, or Firm* — McDermott Will & Emery LLP

(57) ABSTRACT

Embodiments for providing an ultrasound spatial compound image are disclosed. In one embodiment, by way of non-limiting example, an ultrasound system comprises: an ultrasound data acquisition unit configured to acquire ultrasound data by transmitting and receiving ultrasound signals; and a processing unit in communication with the ultrasound data acquisition unit, the processing unit being configured to set a plurality of center lines based on a virtual common point corresponding to predetermined scan-lines, move the virtual common point along each of the center lines to set a plurality of scan-lines, form a plurality of ultrasound images corresponding to the center lines based on the ultrasound data, and perform spatial compounding upon the ultrasound images to form an ultrasound spatial compound image, wherein the ultrasound data acquisition unit is configured to acquire the ultrasound data based on the plurality of scan-lines.

13 Claims, 10 Drawing Sheets

(56) References Cited

U.S. PATENT DOCUMENTS

| | | | |
|---|---|---|---|
| 6,814,701 B1* | 11/2004 | Tamura | 600/443 |
| 7,537,567 B2 | 5/2009 | Jago et al. | |
| 7,632,229 B2 | 12/2009 | Washburn et al. | |
| 2004/0054284 A1* | 3/2004 | Cai et al. | 600/443 |
| 2004/0225218 A1 | 11/2004 | Guracar et al. | |
| 2008/0007115 A1 | 1/2008 | Mizutani | |
| 2008/0064958 A1 | 3/2008 | Ahn et al. | |
| 2008/0071175 A1* | 3/2008 | Lee et al. | 600/443 |
| 2008/0077009 A1 | 3/2008 | Lee et al. | |
| 2008/0088031 A1 | 4/2008 | Kwon et al. | |
| 2008/0200806 A1* | 8/2008 | Liu et al. | 600/439 |
| 2009/0069681 A1 | 3/2009 | Lundberg et al. | |
| 2010/0245353 A1 | 9/2010 | Lee et al. | |

FOREIGN PATENT DOCUMENTS

| | | |
|---|---|---|
| EP | 1 906 207 A1 | 4/2008 |
| JP | 2003-534074 A | 11/2003 |
| JP | 2006-311959 A | 11/2006 |
| JP | 2008-062050 A | 3/2008 |
| JP | 2008-073507 A | 4/2008 |
| JP | 2008-080104 A | 4/2008 |
| KR | 2006-0097474 A | 9/2006 |
| KR | 10-2008-0025903 A | 3/2008 |
| KR | 10-2010-0106633 A | 10/2010 |
| WO | 01-90776 A2 | 11/2001 |

OTHER PUBLICATIONS

Extended European Search Report issued in European Application No. 11177864.3 dated Oct. 14, 2013.

Japanese final Office Action dated Jun. 30, 2015 issued in Japanese Patent Application No. 2011-193119 (English translation).

* cited by examiner

PROVIDING AN ULTRASOUND SPATIAL COMPOUND IMAGE BASED ON CENTER LINES OF ULTRASOUND IMAGES IN AN ULTRASOUND SYSTEM

CROSS-REFERENCE TO RELATED APPLICATION

The present application claims priority from Korean Patent Application No. 10-2010-0101608 filed on Oct. 19, 2010, the entire subject matter of which is incorporated herein by reference.

TECHNICAL FIELD

The present disclosure generally relates to ultrasound systems, and more particularly to providing an ultrasound spatial compound image based on center lines of ultrasound images in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional or three-dimensional ultrasound images of internal features of a target object (e.g., human organs).

The ultrasound system may transmit and receive ultrasound signals to and from a living body to thereby form a 2D (two-dimensional) ultrasound image or a 3D (three-dimensional) ultrasound image. Various techniques have been studied to enhance resolution of the ultrasound image. Spatial compounding is known as one of such techniques.

The spatial compounding is an imaging technique for forming a compound image by combining ultrasound images. That is, the ultrasound system forms a plurality of ultrasound images and performs the spatial compounding upon the ultrasound images to form an ultrasound spatial compound image.

The ultrasound system disposes scan-lines set a virtual common point, at which a plurality of scan-lines intersect, and moves the virtual common point to a particular position to thereby set a plurality of scan-lines corresponding to each of the ultrasound images. However, there is a problem since a steering angle corresponding to a particular scan-line becomes very large and effects of spatial compounding in the center of an image display area for displaying an ultrasound image decrease.

SUMMARY

Embodiments for providing an ultrasound spatial compound image in an ultrasound system are disclosed herein. In one embodiment, by way of non-limiting example, an ultrasound system comprises: an ultrasound data acquisition unit configured to acquire ultrasound data by transmitting and receiving ultrasound signals; and a processing unit in communication with the ultrasound data acquisition unit, the processing unit being configured to set a plurality of center lines on a basis of a virtual common point corresponding to predetermined scan-lines, move the virtual common point along each of the center lines to set a plurality of scan-lines, form a plurality of ultrasound images corresponding to the center lines based on the ultrasound data, and perform spatial compounding upon the ultrasound images to form an ultrasound spatial compound image, wherein the ultrasound data acquisition unit is configured to acquire the ultrasound data based on the plurality of scan-lines.

In another embodiment, there is a method of providing an ultrasound spatial compound image, comprising: a) setting a plurality of center lines based on a virtual common point corresponding to predetermined scan-lines; b) moving the virtual common point along each of the center lines to set a plurality of scan-lines; c) acquiring ultrasound data by transmitting and receiving ultrasound signals based on the plurality of scan-lines; d) forming a plurality of ultrasound images corresponding to the center lines based on the ultrasound data; and e) performing spatial compounding upon the ultrasound images to form an ultrasound spatial compound image.

In yet another embodiment, there is provided a computer readable medium comprising computer executable instructions configured to perform the following acts: a) setting a plurality of center lines based on a virtual common point corresponding to predetermined scan-lines; b) moving the virtual common point along each of the center lines to set a plurality of scan-lines; c) acquiring ultrasound data by transmitting and receiving ultrasound signals based on the plurality of scan-lines; d) forming a plurality of ultrasound images corresponding to the center lines based on the ultrasound data; and e) performing spatial compounding upon the ultrasound images to form an ultrasound spatial compound image.

This summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

First Embodiment

Figure 1:
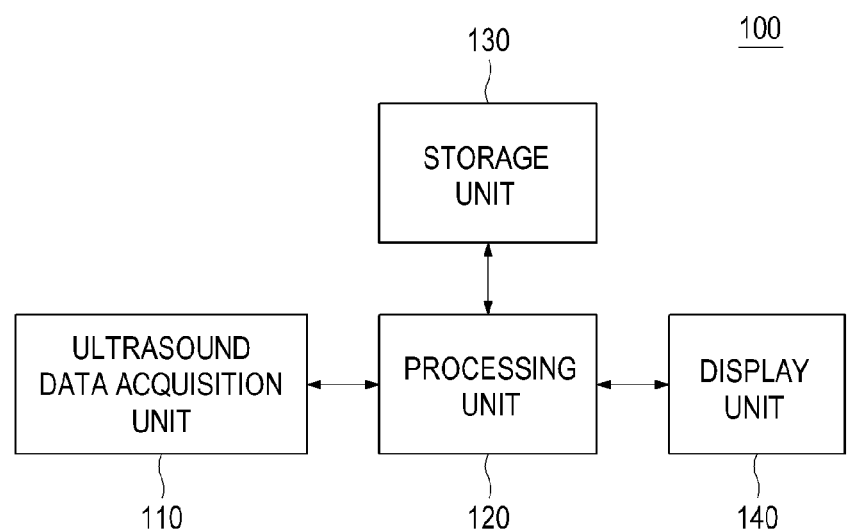
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include an ultrasound data acquisition unit 110. The ultrasound data acquisition unit 110 may be configured to transmit and receive ultrasound signals to and from a living body and output ultrasound data. The living body may include a plurality of target objects (e.g., blood vessels, a heart, etc.).

Figure 2:
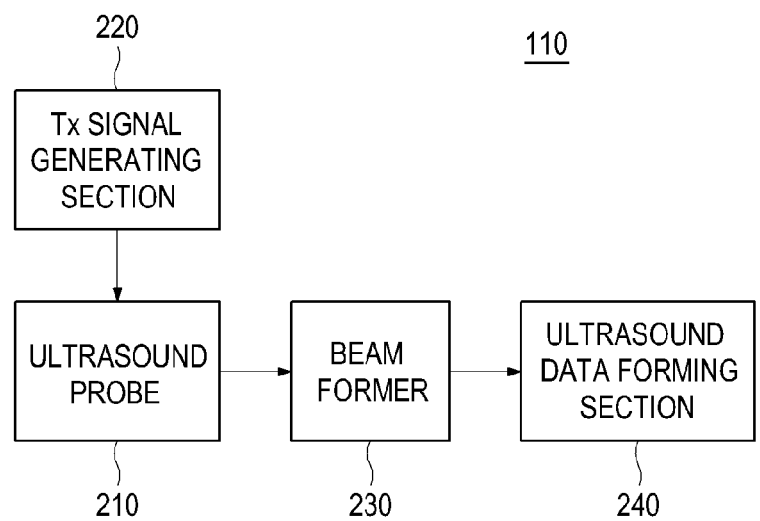
FIG. 2 is a block diagram showing an illustrative embodiment of an ultrasound data acquisition unit.

FIG. 2 is a block diagram showing an illustrative embodiment of the ultrasound data acquisition unit 110. Referring to FIG. 2, the ultrasound data acquisition unit 110 may include an ultrasound probe 210. The ultrasound probe 210 may include a plurality of elements 211 (see FIG. 4) for reciprocally converting between ultrasound signals and electrical signals. The ultrasound probe 210 may be configured to transmit ultrasound signals to the living body along each of the scan-lines. The ultrasound probe 210 may be further configured to receive ultrasound signals (i.e., ultrasound echo signals) from the living body to output received signals. The received signals may be analog signals. The ultrasound probe 210 may include a convex probe. However, it should be noted herein that the ultrasound probe 210 may not be limited thereto.

The ultrasound data acquisition unit 110 may further include a transmit (Tx) signal generating section 220. The Tx signal generating section 220 may be configured to control the transmission of the ultrasound signals. The Tx signal generating section 220 may be further configured to generate electrical signals ("Tx signals") for obtaining at least one ultrasound image in consideration of the elements and focal points. The ultrasound image may include a brightness mode image. However, it should be noted herein that the ultrasound image may not be limited thereto.

Figure 6:
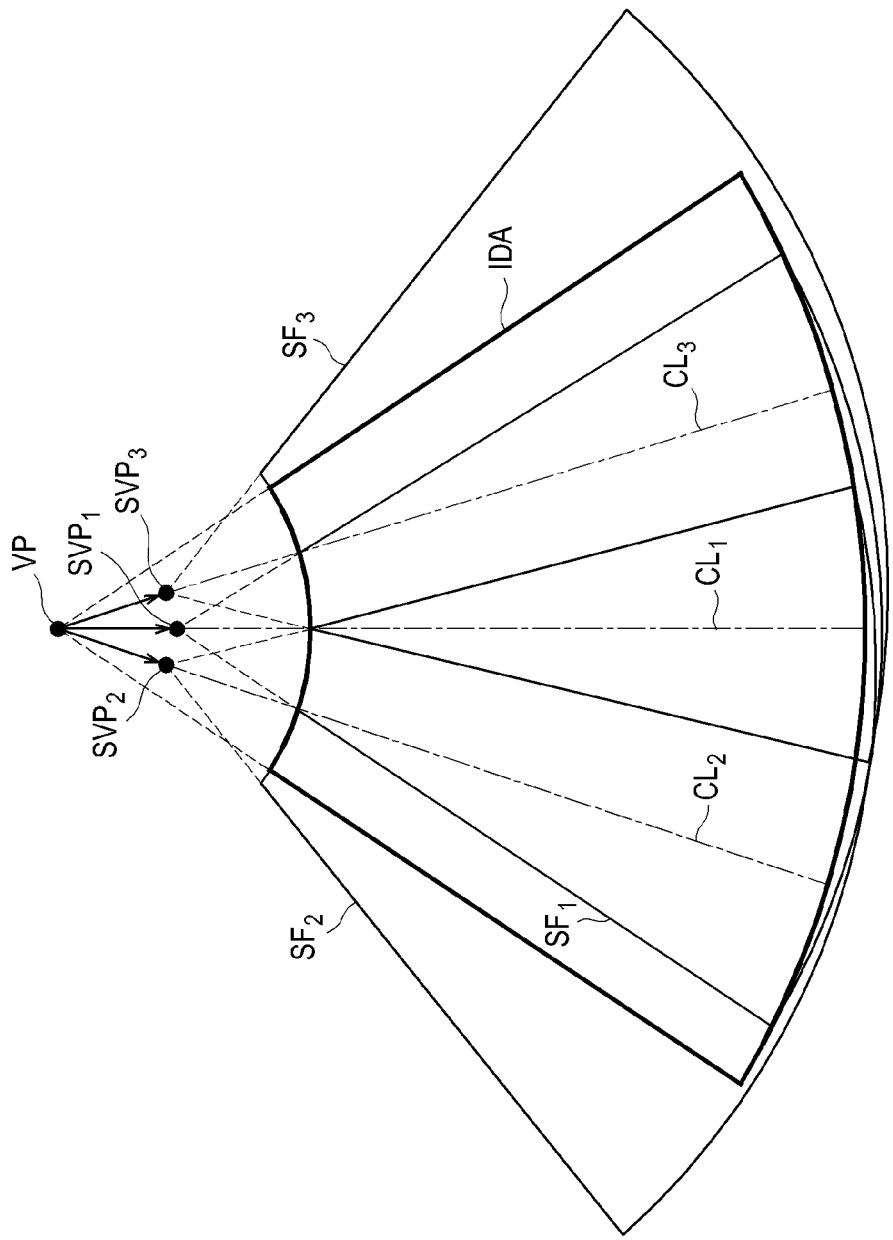
FIG. 6 is a schematic diagram showing an example of sub-virtual common points and ultrasound images in accordance with the first embodiment.

In one embodiment, the Tx signal generating section 220 may be configured to generate first Tx signals for obtaining a first ultrasound image $SF_1$, as shown in FIG. 6. Thus, the ultrasound probe 210 may be configured to convert the first Tx signals provided from the Tx signal generating section 220 into the ultrasound signals, transmit the ultrasound signals to the living body and receive the ultrasound echo signals from the living body to thereby output first received signals. The Tx signal generating section 220 may be further configured to generate second Tx signals for obtaining a second ultrasound image $SF_2$, as shown in FIG. 6. Thus, the ultrasound probe 210 may be configured to convert the second Tx signals provided from the Tx signal generating section 220 into the ultrasound signals, transmit the ultrasound signals to the living body and receive the ultrasound echo signals from the living body to thereby output second received signals. The Tx signal generating section 220 may be further configured to generate third Tx signals for obtaining a third ultrasound image $SF_3$, as shown in FIG. 6. Thus, the ultrasound probe 210 may be configured to convert the third Tx signals provided from the Tx signal generating section 220 into the ultrasound signals, transmit the ultrasound signals to the living body and receive the ultrasound echo signals from the living body to thereby output third received signals.

The number of ultrasound images may be determined depending on the number of the ultrasound images, which are needed to form an ultrasound spatial compound image.

The ultrasound data acquisition unit 110 may further include a beam former 230. The beam former 230 may be configured to convert the received signals provided from the ultrasound probe 210 into digital signals. The beam former 230 may be further configured to apply delays to the digital signals in consideration of the elements and the focal points to thereby output digital receive-focused signals.

In one embodiment, the beam former 230 may be configured to convert the first received signals provided from the ultrasound probe 210 into first digital signals. The beam former 230 may be further configured to apply delays to the first digital signals in consideration of the elements and the focal points to thereby output first digital receive-focused signals. The beam former 230 may be further configured to convert the second received signals provided from the ultrasound probe 210 into second digital signals. The beam former 230 may be further configured to apply delays to the second digital signals in consideration of the elements and the focal points to thereby output second digital receive-focused signals. The beam former 230 may be further configured to convert the third received signals provided from the ultrasound probe 210 into third digital signals. The beam former 230 may be further configured to apply delays to the third digital signals in consideration of the elements and the focal points to thereby output third digital receive-focused signals.

The ultrasound data acquisition unit 110 may further include an ultrasound data forming section 240. The ultrasound data forming section 240 may be configured to form ultrasound data corresponding to the ultrasound image based on the digital receive-focused signals provided from the beam former 230. The ultrasound data may include radio frequency data. However, it should be noted herein that the ultrasound data may not be limited thereto. The ultrasound data forming section 240 may be further configured to perform signal processing (e.g., gain control, etc) upon the digital receive-focused signals.

In one embodiment, the ultrasound data forming section 240 may be configured to form first ultrasound data corresponding to the first ultrasound image $SF_1$ based on the first digital receive-focused signals provided from the beam former 230. The ultrasound data forming section 240 may be further configured to form second ultrasound data corresponding to the second ultrasound image $SF_2$ based on the second digital receive-focused signals provided from the beam former 230. The ultrasound data forming section 240 may be further configured to form third ultrasound data corresponding to the third ultrasound image $SF_3$ based on the third digital receive-focused signals provided from the beam former 230.

Alternatively, the ultrasound data acquisition unit 110 may be further configured to acquire the ultrasound data from an external or internal storage unit (not shown) connected to the ultrasound system 100.

Referring back to FIG. 1, the ultrasound system 100 may further include a processing unit 120 in communication with the ultrasound data acquisition unit 110. The processing unit 120 may include a central processing unit, a microprocessor or a graphic processing unit. However, it should be noted herein that the processing unit 120 may not be limited thereto.

Figure 3:
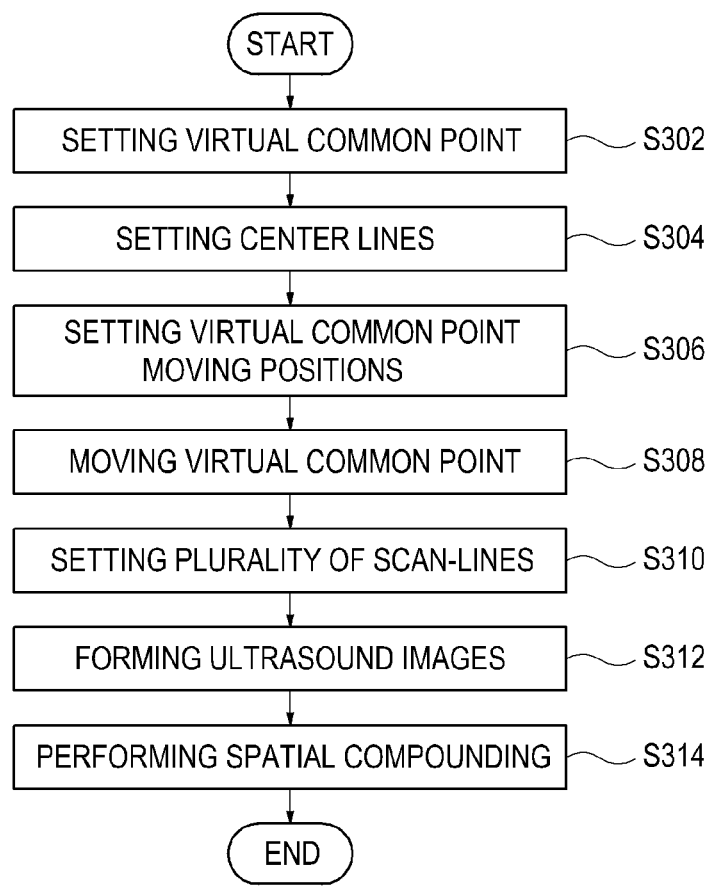
FIG. 3 is a flow chart showing a process of forming an ultrasound spatial compound image in accordance with a first embodiment.
Figure 4:
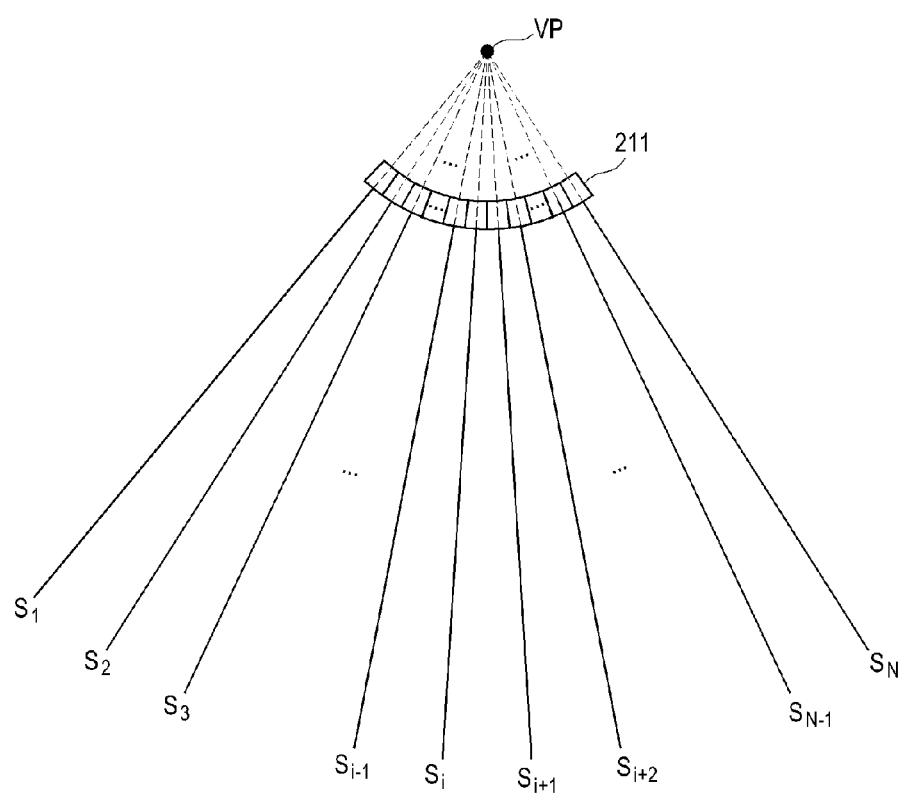
FIG. 4 is a schematic diagram showing an example of a plurality of scan-lines and a virtual common point.

FIG. 3 is a flow chart showing a process of forming an ultrasound spatial compound image in accordance with a first embodiment. The processing unit 120 may be configured to set a virtual common point VP corresponding to scan-lines $S_1$ to $S_N$ in consideration of positions of the elements 211 as shown in FIG. 4, at step S302 in FIG. 3. The virtual common point VP may be a point at which the scan-lines $S_1$ to $S_N$ intersect by extending the scan-lines $S_1$ to $S_N$ to back of the elements 211.

The processing unit 120 may be configured to set center lines corresponding to the ultrasound images based on the virtual common point VP, at step S304 in FIG. 3. Herein, the center lines may converge into the virtual common point VP. Each of the ultrasound images may include a part of an image display area. The image display area may be an area capable of displaying an ultrasound image without steering the scan-lines $S_1$ to $S_N$.

Figure 5:
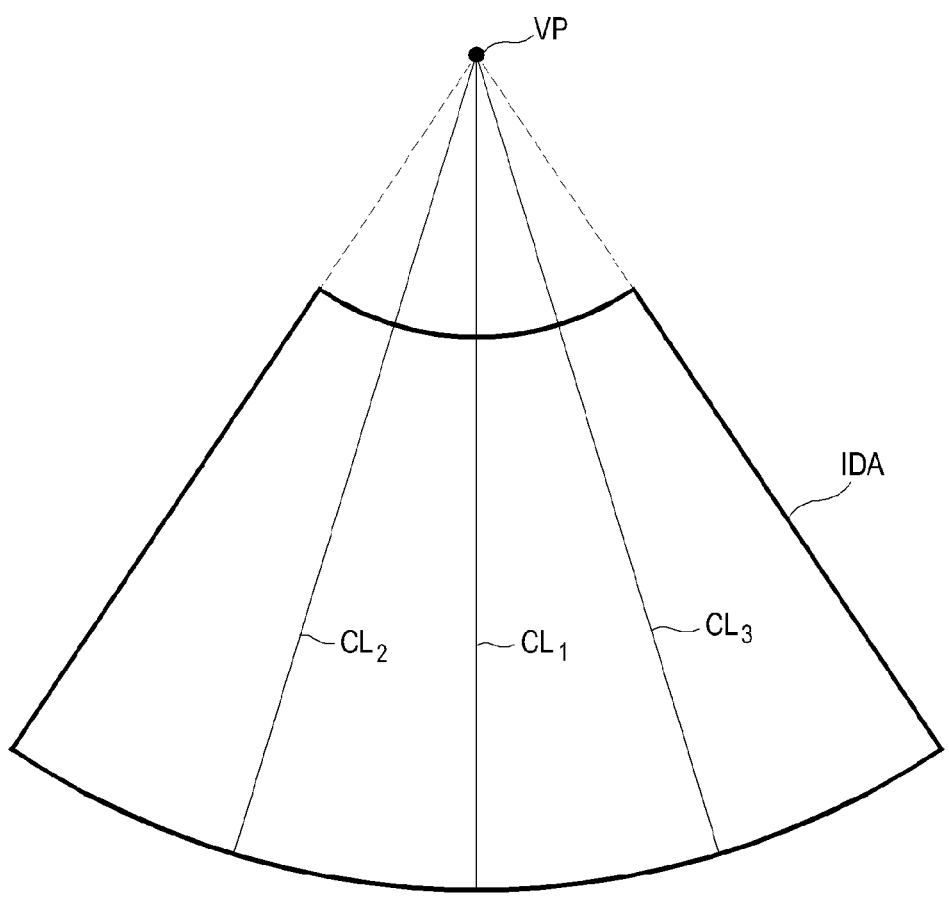
FIG. 5 is a schematic diagram showing an example of setting center lines in accordance with the first embodiment.

In one embodiment, the processing unit 120 may be configured to set a first center line $CL_1$ corresponding to the first ultrasound image $SF_1$, which includes a part of the image display area IDA, based on the virtual common point VP, as shown in FIG. 5. The processing unit 120 may be further configured to set a second center line $CL_2$ corresponding to the second ultrasound image $SF_2$, which includes a part of the image display area IDA, based on the virtual common point VP, as shown in FIG. 5. The processing unit 120 may be further configured to set a third center line $CL_3$ corresponding to the third ultrasound image $SF_3$, which includes a part of the image display area IDA, based on the virtual common point VP, as shown in FIG. 5. Angles between adjacent center lines may be same or different. That is, an angle between the first center line $CL_1$ and the second center line $CL_2$ and an angle between the first center line $CL_1$ and the third center line $CL_3$ may be same or different.

The number of center lines may be determined depending on the number of the ultrasound images to be compounded.

The processing unit 120 may be configured to set virtual common point moving positions corresponding to the center lines based on the virtual common point VP, at step S306 in FIG. 3. The virtual common point moving position may be a position for moving the virtual common point VP to a predetermined distance along a center line in order to form an ultrasound image corresponding to the center line. The processing unit 120 may be configured to move the virtual common point VP to the virtual common point moving positions to set sub-virtual common points corresponding to the ultrasound images, at step S308 in FIG. 3.

The processing unit 120 may be configured to set a first virtual common point moving position for moving the virtual common point VP along the first center line $CL_1$. The processing unit 120 may be further configured to move the virtual common point VP to the first virtual common point moving position to set a first sub-virtual common point $SVP_1$ corresponding to the first ultrasound image $SF_1$, as shown in FIG. 6. The processing unit 120 may be further configured to set a second virtual common point moving position for moving the virtual common point VP along the second center line $CL_2$. The processing unit 120 may be further configured to move the virtual common point VP to the second virtual common point moving position to set a second sub-virtual common point $SVP_2$ corresponding to the second ultrasound image $SF_2$, as shown in FIG. 6. The processing unit 120 may be further configured to set a third virtual common point moving position for moving the virtual common point VP along the third center line $CL_3$. The processing unit 120 may be further configured to move the virtual common point VP to the third common point moving position to set a third sub-virtual common point $SVP_3$ corresponding to the third ultrasound image $SF_3$, as shown in FIG. 6.

The processing unit 120 may be configured to set a plurality of scan-lines corresponding to each of the ultrasound images based on the virtual common point, the sub-virtual common points and the center lines, at step S310 in FIG. 3.

Thus, the ultrasound data acquisition unit 110 may be configured to transmit the ultrasound signals to the living body along the scan-lines and receive the ultrasound echo signals from the living body to acquire the ultrasound data corresponding to each of the ultrasound images.

As one example, the processing unit 120 may be configured to set a reference ultrasound image from the ultrasound images $SF_1$ to $SF_3$. The processing unit 120 may set the first ultrasound image $SF_1$ as the reference ultrasound image. The processing unit 120 may be further configured to detect an element corresponding to the second center line $CL_2$ from the plurality of elements 211 based on the reference ultrasound image. That is, the processing unit 120 may detect the element, through which the second center line $CL_2$ adjacent to the first center line $CL_1$ corresponding to the reference ultrasound image (i.e., first ultrasound image $SF_1$) passes. The processing unit 120 may be further configured to detect a center point of the element. The processing unit 120 may be further configured to set a scan-line, which passes through the center point of the element based on the first sub-virtual common point $SVP_1$ corresponding to the reference ultrasound image, as a reference scan-line (i.e., first scan-line) of the first ultrasound image $SF_1$. The processing unit 120 may be further configured to set a plurality of scan-lines (i.e., steering angles corresponding to of the scan-lines) corresponding to the first ultrasound image $SF_1$ based on the first scan-line of the first ultrasound image $SF_1$. The methods of setting the scan-lines based on the first scan-line are well known in the art. Thus, they have not been described in detail so as not to unnecessarily obscure the present disclosure. The processing unit 120 may be further configured to rotate the first center line $CL_1$ to the second center line $CL_2$ based on the virtual common point VP to set a plurality of scan-lines corresponding to the second ultrasound image $SF_2$. The processing unit 120 may be also configured to rotate the first center line $CL_1$ to the second center line $CL_3$ based on the virtual common point VP to set a plurality of scan-lines corresponding to the third ultrasound image $SF_3$.

As another example, the processing unit 120 may be configured to set a reference ultrasound image from the ultrasound images $SF_1$ to $SF_3$. The processing unit 120 may set the first ultrasound image $SF_1$ as the reference ultrasound image. The processing unit 120 may be further configured to detect an element corresponding to the second center line $CL_2$ from the plurality of elements 211 based on the reference ultrasound image. That is, processing unit 120 may detect the element, through which the second center line $CL_2$ adjacent to the first center line $CL_1$ corresponding to the reference ultrasound image passes. The processing unit 120 may be further configured to detect a center point of the element. The processing unit 120 may be also configured to set a scan-line, which passes through the center point of the element on a basis of the first sub-virtual common point $SVP_1$ corresponding the reference ultrasound image, as a reference scan-line (i.e., last scan-line) of the first ultrasound image $SF_1$ (i.e., reference ultrasound image). The processing unit 120 may be further configured to rotate the first center line $CL_1$ to second center line $CL_2$ based on the virtual common point VP to set a plurality of scan-lines corresponding to the second ultrasound image $SF_2$. The processing unit 120 may be additionally configured to rotate the first center line $CL_1$ to the third center line $CL_3$ based on the virtual common point VP to set a plurality of scan-lines corresponding to the third ultrasound image $SF_3$.

As yet another embodiment, the processing unit 120 may be configured to set a reference ultrasound image from the ultrasound images $SF_1$ to $SF_3$. The processing unit 120 may set the first ultrasound image $SF_1$ as the reference ultrasound image. The processing unit 120 may be further configured to detect a center point of a first element from the plurality of elements 211. The processing unit 120 may be also configured to set a scan-line, which passes through the center point of the first element on a basis of the first sub-virtual common point $SVP_1$, as a reference scan-line (i.e., first scan-line) of the reference ultrasound image. The processing unit 120 may be configured to calculate an angle between the first scan-line $S_1$ shown in FIG. 4 and the first scan-line of the reference ultrasound image. That is, the processing unit 120 may calculate a steering angle of the scan-line $S_1$ shown in FIG. 4 when the virtual common point VP is moved to the first sub-virtual common point $SVP_1$. The processing unit 120 may be further configured to determine whether the calculated angle exists within a predetermined range (e.g., 0<range≤a maximum directivity angle of the ultrasound probe 210). If it is determined that the calculated angle does not exist within the predetermined range, then the processing unit 120 may be further configured to detect a center point of a second element from the plurality of elements 211. The processing unit 120 may be also configured to set a scan-line, which passes through the center point of the second element based on the first sub-virtual common point $SVP_1$, as a first scan-line of the reference ultrasound image (i.e., first ultrasound image $SF_1$). The processing unit 120 may be further configured to calculate an angle between the scan-line $S_2$ shown in FIG. 4 and the first scan-line of the reference ultrasound image. That is, the processing unit 120 may calculate a steering angle of the scan-line $S_2$ shown in FIG. 4 when the virtual common point VP is moved to the first sub-virtual common point $SVP_1$. The processing unit 120 may be further configured to determine whether the calculated angle exists within the predetermined range. If it is determined that the calculated angle exists within the predetermined range, then the processing unit 120 may be further configured to set a plurality of scan-lines (i.e., steering angles corresponding to the scan-lines) of the reference ultrasound image (i.e., first ultrasound image $SF_1$) based on the first scan-line of the reference ultrasound image. The processing unit 120 may be further configured to rotate the first center line $CL_1$ to second center line $CL_2$ based on the virtual common point VP to set a plurality of scan-lines corresponding to the second ultrasound image $SF_2$. The processing unit 120 may be further configured to rotate the first center line $CL_1$ to the third center line $CL_3$ based on the virtual common point VP to set a plurality of scan-lines corresponding to the third ultrasound image $SF_3$.

Although it is described that the processing unit 120 may be configured to set the plurality of scan-lines corresponding to the first ultrasound image based on the first element of the elements 211 and the first scan-line of the first ultrasound image, the processing unit 120 may be further configured to set the plurality of scan-lines corresponding to the first ultrasound image based on the first element of the elements 211 and a last scan-line of the first ultrasound image.

The processing unit 120 may be configured to form the ultrasound images based on the ultrasound data provided from the ultrasound data acquisition unit 110, at step S312 in FIG. 3.

In one embodiment, the processing unit 120 may be configured to form the first ultrasound image $SF_1$ based on the first ultrasound data provided from the ultrasound data acquisition unit 110, as shown in FIG. 6. The processing unit 120 may be further configured to form the second ultrasound image $SF_2$ based on the second ultrasound data provided from the ultrasound data acquisition unit 110, as shown in FIG. 6. The processing unit 120 may be further configured to form the third ultrasound image $SF_3$ based on the third ultrasound data provided from the ultrasound data acquisition unit 110, as shown in FIG. 6.

The processing unit 120 may be configured to perform spatial compounding upon the ultrasound images to form an ultrasound spatial compound image, at step S314 in FIG. 3. The methods of performing the spatial compounding are well known in the art. Thus, they have not been described in detail so as not to unnecessarily obscure the present disclosure. For example, the processing unit 120 may perform the spatial compounding by calculating a mean brightness value corresponding to each of the pixels of the ultrasound images.

Referring back to FIG. 1, the ultrasound system 100 may further include a storage unit 130. The storage unit 130 may store the ultrasound data acquired by the ultrasound data acquisition unit 110. The storage unit 130 may further store the ultrasound images formed by the processing unit 120.

The ultrasound system 100 may further include a display unit 140. The display unit 140 may be configured to display the ultrasound spatial compound image. The display unit 140 may be also configured to display the ultrasound images.

Second Embodiment

Referring to FIG. 2, the ultrasound probe 210 may include the plurality of elements 211 (see FIG. 4) for reciprocally converting between ultrasound signals and electrical signals. The ultrasound probe 210 may be configured to transmit the ultrasound signals to the living body along the scan-lines. The ultrasound probe 210 may be further configured to receive the ultrasound echo signals from the living body to output the received signals.

The Tx signal generating section 220 may be configured to control the transmission of the ultrasound signals. The Tx signal generating section 220 may be further configured to generate the Tx signals for obtaining at least one ultrasound image in consideration of the elements and the focal points.

Figure 9:
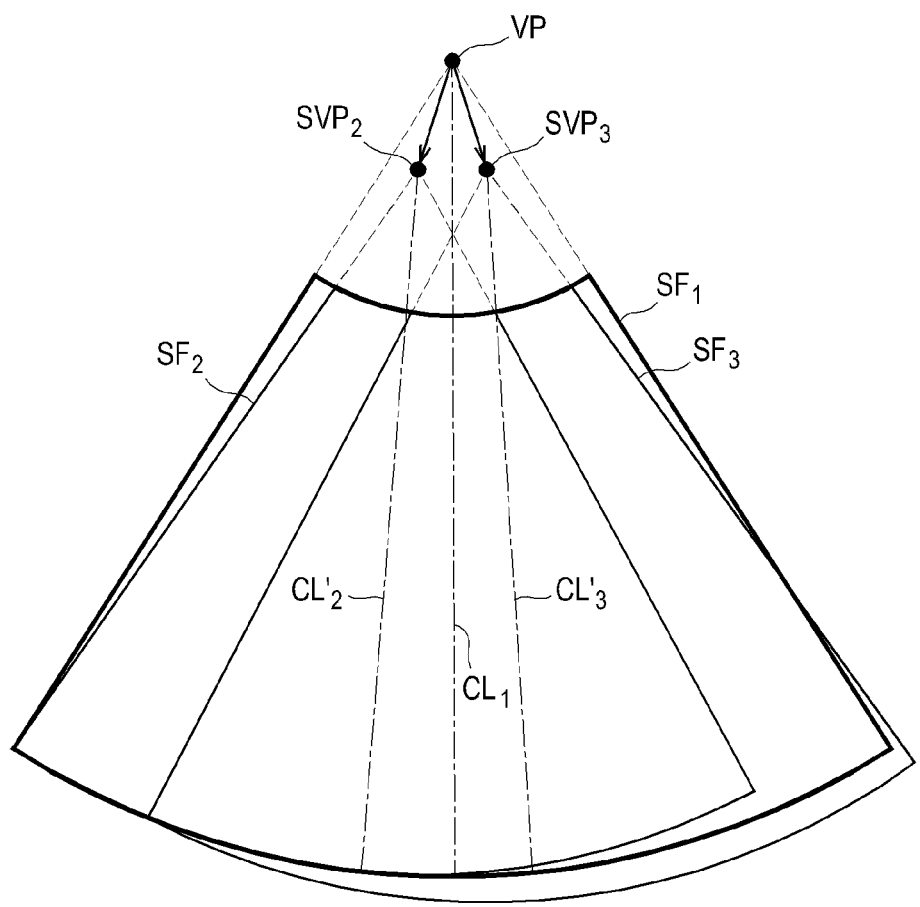
FIG. 9 is a schematic diagram showing an example of sub-virtual common point and ultrasound images in accordance with the second embodiment.

The Tx signal generating section 220 may be configured to generate first Tx signals for obtaining a first ultrasound image $SF_1$, as shown in FIG. 9. Thus, the ultrasound probe 210 may be configured to convert the first Tx signals provided from the Tx signal generating section 220 into the ultrasound signals, transmit the ultrasound signals to the living body and receive the ultrasound echo signals from the living body to thereby output first received signals. The Tx signal generating section 220 may be further configured to generate second Tx signals for obtaining a second ultrasound image $SF_2$, as shown in FIG. 9. Thus, the ultrasound probe 210 may be configured to convert the second Tx signals provided from the Tx signal generating section 220 into the ultrasound signals, transmit the ultrasound signals to the living body and receive the ultrasound echo signals from the living body to thereby output second received signals. The Tx signal generating section 220 may be further configured to generate third Tx signals for obtaining a third ultrasound image $SF_3$, as shown in FIG. 9. Thus, the ultrasound probe 210 may be configured to convert the third Tx signals provided from the Tx signal generating section 220 into the ultrasound signals, transmit the ultrasound signals to the living body and receive the ultrasound echo signals from the living body to thereby output third received signals.

The beam former 230 may be configured to convert the received signals provided from the ultrasound probe 210 into digital signals. The beam former 230 may be further configured to apply delays to the digital signals in consideration of the elements and the focal points to thereby output digital receive-focused signals.

In one embodiment, the beam former 230 may be configured to convert the first received signals provided from the ultrasound probe 210 into first digital signals. The beam former 230 may be further configured to apply delays to the first digital signals in consideration of the elements and the focal points to thereby output first digital receive-focused signals. The beam former 230 may be further configured to convert the second received signals provided from the ultrasound probe 210 into second digital signals. The beam former 230 may be also configured to apply delays to the second digital signals in consideration of the elements and the focal points to thereby output second digital receive-focused signals. The beam former 230 may be further configured to convert the third received signals provided from the ultrasound probe 210 into third digital signals. The beam former 230 may be also configured to apply delays to the third digital signals in consideration of the elements and the focal points to thereby output third digital receive-focused signals.

The ultrasound data forming section 240 may be configured to form ultrasound data based on the digital receive-focused signals provided from the beam former 230. The ultrasound data may include radio frequency data. However, it should be noted herein that the ultrasound data may not be limited thereto. The ultrasound data forming section 240 may be further configured to perform signal processing (e.g., gain control, etc) upon the digital receive-focused signals.

The ultrasound data forming section 240 may be configured to form first ultrasound data corresponding to the first ultrasound image $SF_1$ shown in FIG. 9 based on the first digital receive-focused signals provided from the beam former 230. The ultrasound data forming section 240 may be further configured to form second ultrasound data corresponding to the second ultrasound image $SF_2$ shown in FIG. 9 based on the second digital receive-focused signals provided from the beam former 230. The ultrasound data forming section 240 may be also configured to form third ultrasound data corresponding to the third ultrasound image $SF_3$ shown in FIG. 9 based on the third digital receive-focused signals provided from the beam former 230.

Figure 7:
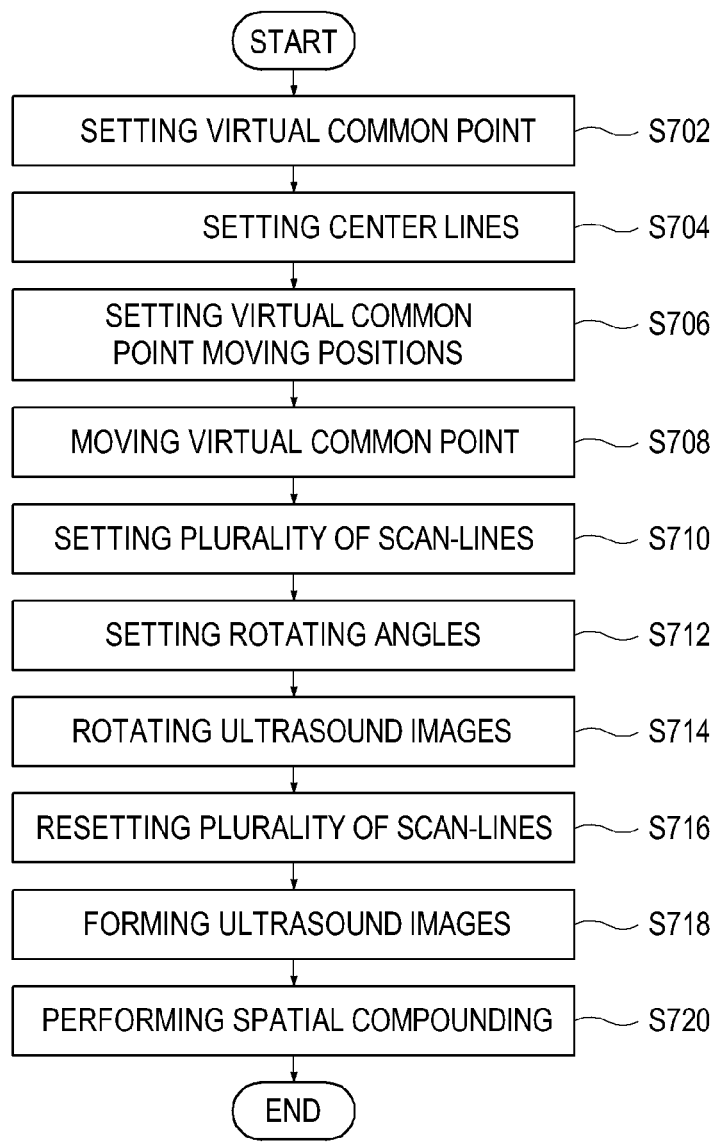
FIG. 7 is a flow chart showing a process of forming an ultrasound spatial compound image in accordance with a second embodiment.

FIG. 7 is a flow chart showing a process of forming an ultrasound spatial compound image in accordance with a second embodiment. The processing unit 120 may be configured to set the virtual common point VP corresponding to the scan-lines $S_1$ to $S_N$ in consideration of positions of the elements 211 as shown in FIG. 4, at step S702 in FIG. 7.

The processing unit 120 may be configured to set center lines corresponding to the ultrasound images based on the virtual common point VP, at step S704 in FIG. 7.

Figure 8:
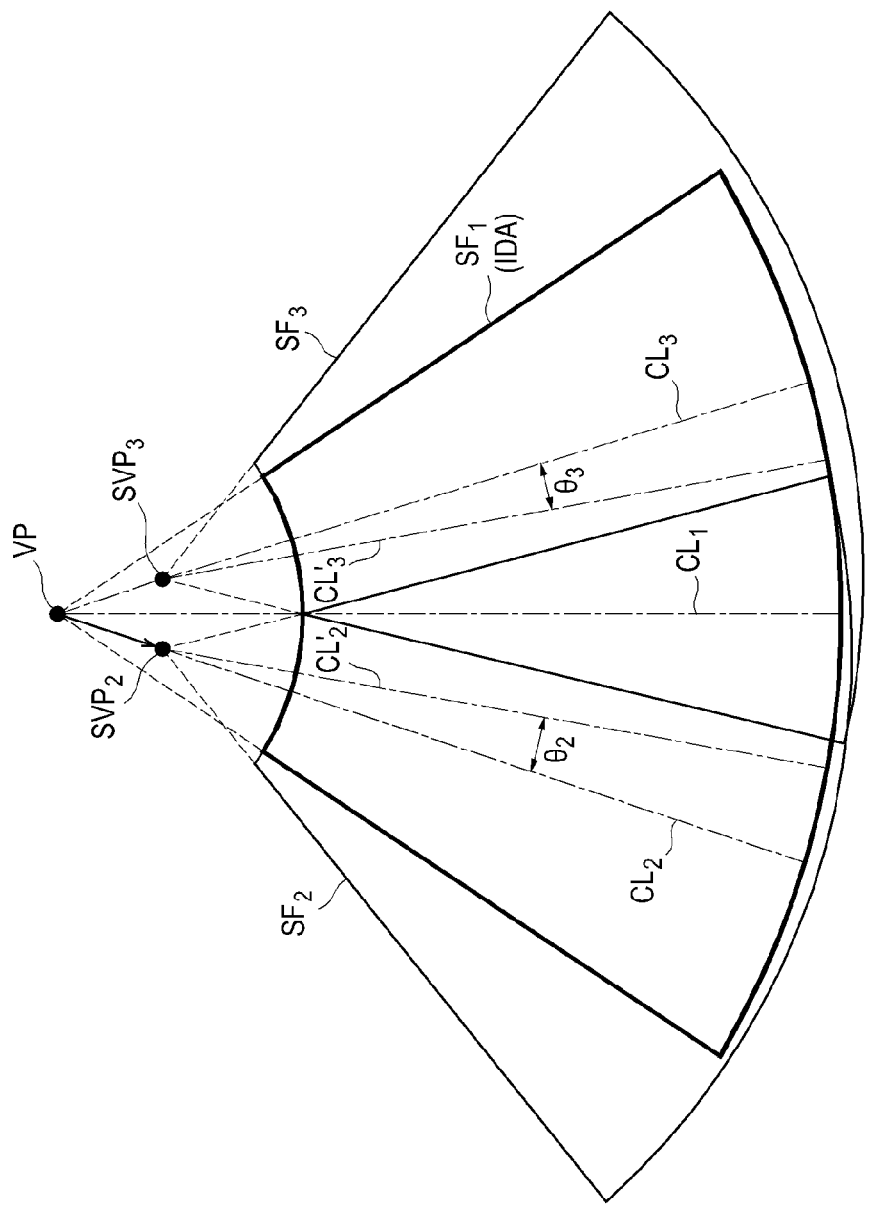
FIG. 8 is a schematic diagram showing an example of setting center lines in accordance with the second embodiment.

In one embodiment, the processing unit 120 may be configured to set a first center line $CL_1$ corresponding to the first ultrasound image $SF_1$, which includes the image display area IDA, based on the virtual common point VP as shown in FIG. 8. The processing unit 120 may be further configured to set a second center line $CL_2$ corresponding to the second ultrasound image $SF_2$, which includes a part of the image display area IDA, based on the virtual common point VP, as shown in FIG. 8. The processing unit 120 may be also configured to set a third center line $CL_3$ corresponding to the third ultrasound image $SF_3$, which includes a part of the image display area IDA, based on the virtual common point VP as shown in FIG. 8. Angles between adjacent center lines may be same or different. That is, an angle between the first center line $CL_1$ and the second center line $CL_2$ and an angle between the first center line $CL_1$ and the third center line $CL_3$ may be same or different.

The number of center lines may be determined depending on the number of the ultrasound images to be compounded.

The processing unit 120 may be configured to set virtual common point moving positions corresponding to the center lines based on the virtual common point VP, at step S706 in FIG. 7. The processing unit 120 may be configured to move the virtual common point VP to the virtual common point moving positions to set sub-virtual common points corresponding to the ultrasound images, at step S708 in FIG. 7.

In one embodiment, the processing unit 120 may be configured to set a first virtual common point moving position for moving the virtual common point VP along the first center line $CL_1$. The first virtual common point moving position corresponds to the virtual common point VP. That is, the processing unit 120 may set the first virtual common point moving position, to which the virtual common point VP is not moved, in order to obtain the first ultrasound image $SF_1$. The first ultrasound image $SF_1$ may be set as a reference ultrasound image. The processing unit 120 may be further configured to set a second virtual common point moving position for moving the virtual common point VP along the second center line $CL_2$. The processing unit 120 may be also configured to move the virtual common point VP to the second virtual common point moving position to set a second sub-virtual common point $SVP_2$ corresponding to the second ultrasound image $SF_2$, as shown in FIG. 8. The processing unit 120 may be further configured to set a third virtual common point moving position for moving the virtual common point VP along the center line $CL_3$. The processing unit 120 may be further configured to move the virtual common point VP to the third virtual common point moving position to set a third sub-virtual common point $SVP_3$ corresponding to the third ultrasound image $SF_3$, as shown in FIG. 8.

The processing unit 120 may be configured to set a plurality of scan-lines corresponding to each of the ultrasound images based on the virtual common point, the sub-virtual common points and the center lines, at step S710 in FIG. 7. Thus, the ultrasound data acquisition unit 110 may be configured to transmit the ultrasound signals to the living body along the scan-lines and receive the ultrasound echo signals from the living body to acquire the ultrasound data corresponding to each of the ultrasound images.

As one example, the processing unit 120 may be configured to set a plurality of scan-lines corresponding to the first ultrasound image $SF_1$ based on the virtual common point VP. The scan-lines of the first ultrasound image $SF_1$ correspond to the scan-lines $S_1$ to $S_N$ shown in FIG. 4. The processing unit 120 may be further configured to detect an element corresponding to the second center line $CL_2$ from the plurality of elements 211. That is, the processing unit 120 may detect the element, through which the second center line $CL_2$ passes, from the plurality of elements 211. The processing unit 120 may be further configured to detect a center point of the element. The processing unit 120 may be also configured to rotate the second center line $CL_2$ to the first center line $CL_1$ based on the virtual common point VP. The processing unit 120 may be further configured to set a scan-line, which passes through the center point of the element, as a first scan-line of the second ultrasound image $SF_2$ based on the second sub-virtual common point $SVP_2$. The processing unit 120 may be also configured to set a plurality of scan-lines (i.e., steering angles corresponding to the scan-lines) corresponding to the second ultrasound image $SF_2$ based on the first scan-line of the second ultrasound image $SF_2$. The methods of setting the scan-lines based on the first scan-line are well known in the art. Thus, they have not been described in detail so as not to unnecessarily obscure the present disclosure. The processing unit 120 may be further configured to reconvey the second center line $CL_2$ based on the virtual common point VP. The processing unit 120 may be further configured to detect an element corresponding to the third center line $CL_3$ from the plurality of elements 211. That is, the processing unit 120 may detect the element, through which the third center line $CL_3$ passes, from the plurality of elements 211. The processing unit 120 may be further configured to detect a center point of the element. The processing unit 120 may be also configured to rotate the third center line $CL_3$ to the first center line $CL_1$ based on the virtual common point VP. The processing unit 120 may be further configured to set a scan-line, which passes through the center point of the element as a first scan-line of the third ultrasound image $SF_3$ based on the third sub-virtual common point $SVP_3$. The processing unit 120 may be further configured to set a plurality of scan-lines (i.e., steering angles corresponding to the scan-lines) corresponding to the third ultrasound image $SF_3$ based on the first scan-line of the third ultrasound image $SF_3$. The processing unit 120 may be configured to reconvey the third center line $CL_3$ based on the virtual common point VP.

As another example, the processing unit 120 may be configured to set a plurality of scan-lines corresponding to the first ultrasound image $SF_1$ based on the virtual common point VP. The scan-lines of the first ultrasound image $SF_1$ correspond to the scan-lines $S_1$ to $S_N$ shown in FIG. 4. The processing unit 120 may be further configured to detect an element corresponding to the second center line $CL_2$ from the plurality of elements 211. That is, the processing unit 120 may detect the element, through which the second center line $CL_2$ passes, from the plurality of elements 211. The processing unit 120 may be further configured to detect a center point of the element. The processing unit 120 may be further configured to rotate the second center line $CL_2$ to the first center line $CL_1$ based on the virtual common point VP. The processing unit 120 may be further configured to set a scan-line, which passes through the center point of the element, as a reference scan-line (i.e., last scan-line) of the second ultrasound image $SF_2$ based on the second sub-virtual common point $SVP_2$. The processing unit 120 may be further configured to set a plurality of scan-lines (i.e., steering angles corresponding to the scan-lines) corresponding to the second ultrasound image $SF_2$ based on the last scan-line of the second ultrasound image $SF_2$. The methods of setting the scan-lines based on the last scan-line are well known in the art. Thus, they have not been described in detail so as not to unnecessarily obscure the present disclosure. The processing unit 120 may be further configured to reconvey the second center line $CL_2$ based on the virtual common point VP. The processing unit 120 may be further configured to detect an element corresponding to the third center line $CL_3$ from the plurality of elements 211. That is, the processing unit 120 may detect the element, through which the third center line $CL_3$ passes, from the plurality of elements 211. The processing unit 120 may be further configured to detect a center point of the element. The processing unit 120 may be also configured to rotate the third center line $CL_3$ to first center line $CL_1$ based on the virtual common point VP. The processing unit 120 may be further configured to set a scan-line, which passes through the center point of the element as a last scan-line of the third ultrasound image $SF_3$ based on the third sub-virtual common point $SVP_3$. The processing unit 120 may be further configured to set a plurality of scan-lines (i.e., steering angles corresponding to the scan-lines) corresponding to the third ultrasound image $SF_3$ based on the last scan-line of the third ultrasound image $SF_3$. The processing unit 120 may be further configured to reconvey the third center line $CL_3$ based on the virtual common point VP.

As yet another example, the processing unit 120 may be configured to set a plurality of scan-lines corresponding to the first ultrasound image $SF_1$ based on the virtual common point VP. The scan-lines of the first ultrasound image $SF_1$ correspond to the scan-lines $S_1$ to $S_N$ shown in FIG. 4. The processing unit 120 may be further configured to rotate the second center line $CL_2$ to the first center line $CL_1$ based on the virtual common point VP. The processing unit 120 may be further configured to detect a center point of a first element from the plurality of elements 211. The processing unit 1120 may be further configured to set a scan-line, which passes through the center point of the first element, as a reference scan-line (i.e., first scan-line) of the second ultrasound image $SF_2$ based on the second sub-virtual common point $SVP_2$. The processing unit 120 may be further configured to calculate an angle between the scan-line $S_1$ shown in FIG. 4 and the first scan-line of the second ultrasound image $SF_2$. The processing unit 120 may be further configured to determine whether the calculated angle exists within a predetermined range (e.g., 0<range≤a maximum directivity angle of the ultrasound probe 210). If it is determined that the calculated angle does not exist within the predetermined range, then the processing unit 120 may be further configured to detect a center point of a second element from the plurality of elements 211. The processing unit 120 may be further configured to set a scan-line, which passes through the center point of the second element on a basis of the second sub-virtual common point $SVP_2$, as the first scan-line of the second ultrasound image $SF_2$. The processing unit 120 may be also configured to calculate an angle between the scan-line $S_2$ shown in FIG. 4 and the first scan-line of the second ultrasound image $SF_2$. The processing unit 120 may be further configured to determine whether the calculated angle exists within the predetermined range. If it is determined that the calculated angle exists within the predetermined angle, then the processing unit 120 may be further configured to set a plurality of scan-lines corresponding to the second ultrasound image $SF_2$ based on the first scan-line of the second ultrasound image $SF_2$. The processing unit 120 may be further configured to set a plurality of scan-lines corresponding to the third ultrasound image $SF_3$, as mentioned above.

Although it is described that the processing unit 120 may be configured to set the plurality of scan-lines based on the first element and the first scan-line, the processing unit 120 may be further configured to set the plurality of scan-lines based on a last element and a last scan-line.

The processing unit 120 may be configured to set rotating angles corresponding to the center lines, at step S712 in FIG. 7. The rotating angle is an angle for the ultrasound images including the part of the image display area IDA into the image display area IDA.

In one embodiment, the processing unit 120 may be configured to set a first rotating angle corresponding to the first center line $CL_1$ based on the first sub-virtual common point (i.e., virtual common point VP). The first rotating angle is an angle for rotating the first ultrasound image $SF_1$ into the image display area IDA based on the first sub-virtual common point, and is 0. The processing unit 120 may be further configured to set a second rotating angle $\theta_2$ corresponding to the second center line $CL_2$ based on the second sub-virtual common point $SVP_2$ as shown in FIG. 8. The second rotating angle $\theta_2$ is an angle for rotating the second ultrasound image $SF_2$ into the image display area IDA based on the second sub-virtual common point $SVP_2$. The processing unit 120 may be further configured to set a third rotating angle $\theta_2$ corresponding to the third center line $CL_3$ based on the third sub-virtual common point $SVP_3$ as shown in FIG. 8. The third rotating angle $\theta_3$ is an angle for rotating the third ultrasound image $SF_3$ into the image display area IDA based on the third sub-virtual common point $SVP_3$.

The processing unit 120 may be configured to rotate the ultrasound images into the image display area IDA based on the rotating angles and the sub-virtual common points, at step S714 in FIG. 7.

In one embodiment, the processing unit 120 may be configured to rotate the second center line $CL_2$ to a new second center line $CL_2'$ corresponding to the second rotating angle $\theta_2$ based on the second sub-virtual common point $SVP_2$, as shown in FIG. 9. Thus, the second ultrasound image $SF_2$ may be rotated into the image display area IDA, as shown in FIG. 9. The processing unit 120 may be further configured to rotate the third center line $CL_3$ to a new third center line $CL_3'$ corresponding to the third rotating angle $\theta_3$ based on the third sub-virtual common point $SVP_3$, as shown in FIG. 9. Thus, the third ultrasound image $SF_3$ may be rotated into the image display area IDA, as shown in FIG. 9.

The processing unit 120 may be configured to reset a plurality of scan-lines corresponding to each of the ultrasound images based on the rotating angles, at step S716 in FIG. 7. Thus, the ultrasound data acquisition unit 110 may be configured to transmit the ultrasound signals to the living body along the reset scan-lines and receive the ultrasound echo signals from the living body to thereby acquire the ultrasound data corresponding to each of the ultrasound images.

In one embodiment, the processing unit 120 may be configured to reset the plurality of scan-lines corresponding to the second ultrasound image $SF_2$, which is rotated into the image display area IDA based on the second rotating angle $\theta_2$. The processing unit 120 may be further configured to reset the plurality of scan-lines corresponding to the third ultrasound image $SF_3$, which is rotated into the image display area IDA based on the third rotating angle $\theta_3$.

The processing unit 120 may be configured to form the ultrasound images based on the ultrasound data provided from the ultrasound data acquisition unit 110, at step S718 in FIG. 7.

In one embodiment, the processing unit 120 may be configured to form the first ultrasound image $SF_1$ based on the first ultrasound data provided from the ultrasound data acquisition unit 110, as shown in FIG. 9. The processing unit 120 may be further configured to form the second ultrasound image $SF_2$ based on the second ultrasound data provided from the ultrasound data acquisition unit 110, as shown in FIG. 9. The processing unit 120 may be further configured to form the third ultrasound image $SF_3$ based on the third ultrasound data provided from the ultrasound data acquisition unit 110, as shown in FIG. 9.

The processing unit 120 may be configured to perform spatial compounding upon the ultrasound images to form an ultrasound spatial compound image, at step S720 in FIG. 7. The methods of performing the spatial compounding are well known in the art. Thus, they have not been described in detail so as not to unnecessarily obscure the present disclosure. For example, the processing unit 120 may perform the spatial compounding by calculating a mean brightness value corresponding to each of the pixels of the ultrasound images.

Third Embodiment

Referring to FIG. 2, the ultrasound probe 210 may include a plurality of elements 211 (see FIG. 4) for reciprocally converting between ultrasound signals and electrical signals. The ultrasound probe 210 may be configured to transmit ultrasound signals to the living body along the scan-lines. The ultrasound probe 210 may be further configured to receive ultrasound signals (i.e., ultrasound echo signals) from the living body to output received signals. The received signals may be analog signals. The ultrasound probe 210 may include a wide view angle probe. However, it should be noted herein that the ultrasound probe 210 may not be limited thereto.

The Tx signal generating section 220 may be configured to control the transmission of the ultrasound signals. The Tx signal generating section 220 may be further configured to generate the Tx signals for obtaining at least one ultrasound image in consideration of the elements and the focal points.

Figure 11:
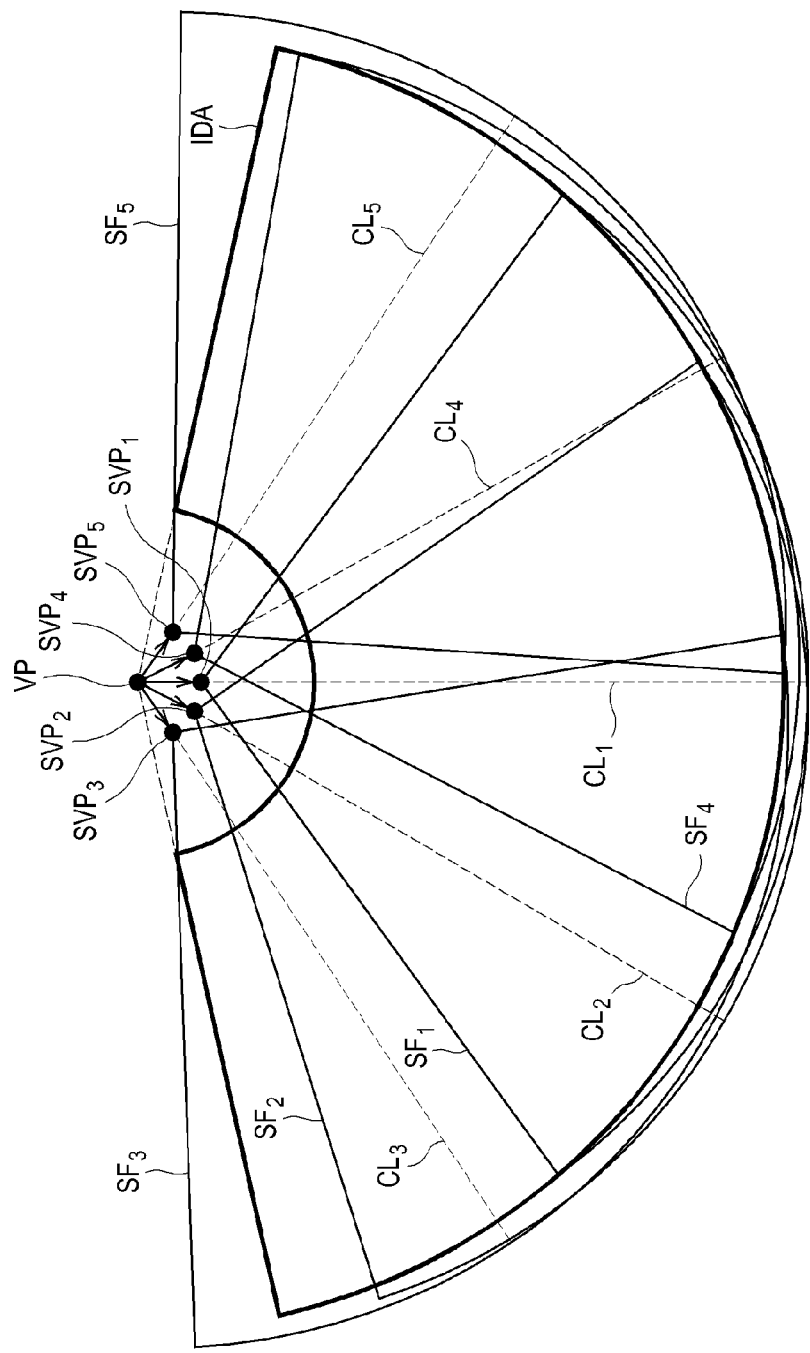
FIG. 11 is a schematic diagram showing an example of center lines, sub-virtual common points and ultrasound images in accordance with the third embodiment.

In one embodiment, the Tx signal generating section 220 may be configured to generate first Tx signals for obtaining a first ultrasound image $SF_1$ shown in FIG. 11. Thus, the ultrasound probe 210 may be configured to convert the first Tx signals provided from the Tx signal generating section 220 into the ultrasound signals, transmit the ultrasound signals to the living body and receive the ultrasound echo signals from the living body to thereby output first received signals. The Tx signal generating section 220 may be further configured to generate second Tx signals for obtaining a second ultrasound image $SF_2$ shown in FIG. 11. Thus, the ultrasound probe 210 may be configured to convert the second Tx signals provided from the Tx signal generating section 220 into the ultrasound signals, transmit the ultrasound signals to the living body and receive the ultrasound echo signals from the living body to thereby output second received signals. The Tx signal generating section 220 may be further configured to generate third Tx signals for obtaining a third ultrasound image $SF_3$ shown in FIG. 11. As such, the ultrasound probe 210 may be configured to convert the third Tx signals provided from the Tx signal generating section 220 into the ultrasound signals, transmit the ultrasound signals to the living body and receive the ultrasound echo signals from the living body to thereby output third received signals. The Tx signal generating section 220 may be further configured to generate fourth Tx signals for obtaining a fourth ultrasound image $SF_4$ shown in FIG. 11. Thus, the ultrasound probe 210 may be configured to convert the fourth Tx signals provided from the Tx signal generating section 220 into the ultrasound signals, transmit the ultrasound signals to living body and receive the ultrasound echo signals from the living body to thereby output fourth received signals. The Tx signal generating section 220 may be further configured to generate fifth Tx signals for obtaining a fifth ultrasound image $SF_5$ shown in FIG. 11. Accordingly, the ultrasound probe 210 may be configured to convert the fifth Tx signals provided from the Tx signal generating section 220 into the ultrasound signals, transmit the ultrasound signals to the living body and receive the ultrasound echo signals from the living body to thereby output fifth received signals.

The beam former 230 may be configured to convert the received signals provided from the ultrasound probe 210 into digital signals. The beam former 230 may be further configured to apply delays to the digital signals in consideration of the elements and the focal points to thereby output digital receive-focused signals.

In one embodiment, the beam former 230 may be configured to convert the first received signals provided from the ultrasound probe 210 into first digital signals. The beam former 230 may be further configured to apply delays to the first digital signals in consideration of the elements and the focal points to thereby output first digital receive-focused signals. The beam former 230 may be further configured to convert the second received signals provided from the ultrasound probe 210 into second digital signals. The beam former 230 may be further configured to apply delays to the second digital signals in consideration of the elements and the focal points to thereby output second digital receive-focused signals. The beam former 230 may be further configured to convert the third received signals provided from the ultrasound probe 210 into third digital signals. The beam former 230 may be also configured to apply delays to the third digital signals in consideration of the elements and the focal points to thereby output third digital receive-focused signals. The beam former 230 may be further configured to covert the fourth received signals provided from the ultrasound probe 210 into fourth digital signals. The beam former 230 may be further configured to apply delays to the fourth digital signals in consideration of the elements and the focal points to thereby output fourth digital receive-focused signals. The beam former 230 may be additionally configured to convert the fifth received signals provided from the ultrasound probe 210 into fifth digital signals. The beam former 230 may be further configured to apply delays to the fifth digital signals in consideration of the elements and the focal points to thereby output fifth digital receive-focused signals.

The ultrasound data forming section 240 may be configured to form ultrasound data based on the digital receive-focused signals provided from the beam former 230. The ultrasound data may include radio frequency data. However, it should be noted herein that the ultrasound data may not be limited thereto. The ultrasound data forming section 240 may be further configured to perform the signal processing (e.g., gain control, etc) upon the digital receive-focused signals.

In one embodiment, the ultrasound data forming section 240 may be configured to form first ultrasound data corresponding to the first ultrasound image $SF_1$ shown in FIG. 11 based on the first digital receive-focused signals. The ultrasound data forming section 240 may be further configured to form second ultrasound data corresponding to the second ultrasound image $SF_2$ shown in FIG. 11 based on the second digital receive-focused signals. The ultrasound data forming section 240 may be also configured to form third ultrasound data corresponding to the third ultrasound image $SF_3$ shown in FIG. 11 based on the third digital receive-focused signals. The ultrasound data forming section 240 may be further configured to form fourth ultrasound data corresponding to the fourth ultrasound image $SF_4$ shown in FIG. 11 based on the fourth digital receive-focused signals. The ultrasound data forming section 240 may be configured to form fifth ultrasound data corresponding to fifth ultrasound image $SF_5$ shown in FIG. 11 based on the fifth digital receive-focused signals.

Figure 10:
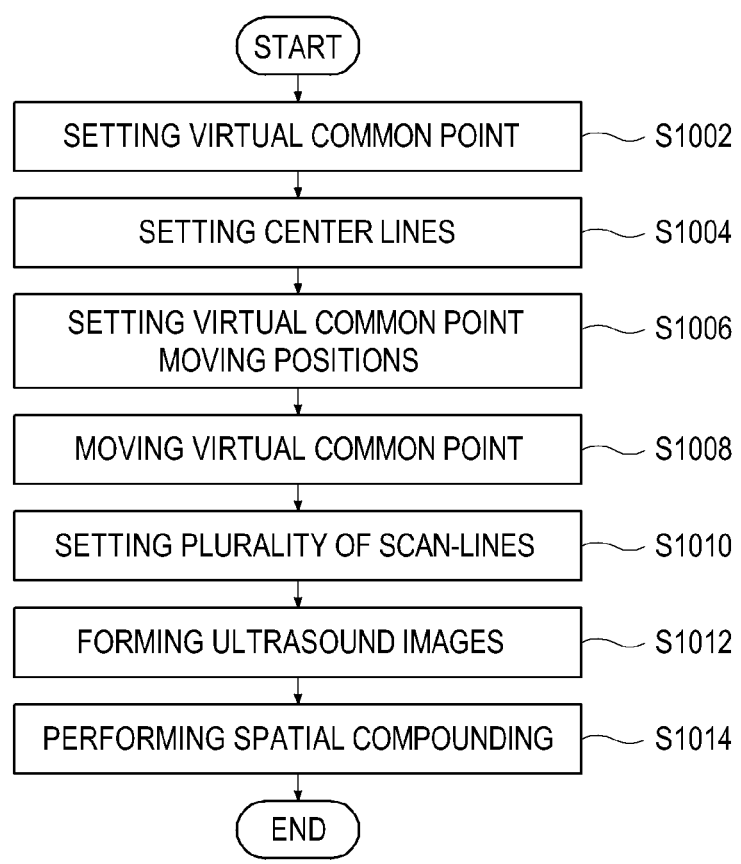
FIG. 10 is a flow chart showing a process of forming an ultrasound spatial compound image in accordance with a third embodiment.

FIG. 10 is a flow chart showing a process of forming an ultrasound spatial compound image in accordance with a third embodiment. The processing unit 120 may be configured to set the virtual common point VP corresponding to the scan-lines $S_1$ to $S_N$ in consideration of positions of the elements 211 as shown in FIG. 4, at step S1002 in FIG. 10.

The processing unit 120 may be configured to center lines corresponding to the ultrasound images on a basis of the virtual common point VP, at step S1004 in FIG. 10.

In one embodiment, the processing unit 120 may be configured to set a first center line $CL_1$ corresponding to the first ultrasound image $SF_1$, which includes a part of the image display area IDA, based on the virtual common point VP as shown in FIG. 11. The processing unit 120 may be further configured to set a second center line $CL_2$ corresponding to the second ultrasound image $SF_2$, which includes a part of the image display area IDA, based on the virtual common point VP as shown in FIG. 11. The processing unit 120 may be further configured to set a third center line $CL_3$ corresponding to the third ultrasound image $SF_3$, which includes a part of the image display area IDA, based on the virtual common point VP as shown in FIG. 11. The processing unit 120 may be also configured to set a fourth center line $CL_4$ corresponding to the fourth ultrasound image $SF_4$, which includes a part of the image display area IDA, based on the virtual common point VP as shown in FIG. 11. The processing unit 120 may be further configured to set a fifth center line $CL_5$ corresponding to the fifth ultrasound image $SF_5$, which includes a part of the image display area IDA, based on the virtual common point VP as shown in FIG. 11. Angles between the adjacent center lines may be same or different. That is, an angle between the first center line $CL_1$ and the second center line $CL_2$, an angle between the second center line $CL_2$ and the third center line $CL_3$, an angle between the first center line $CL_1$ and the fourth center line $CL_4$, and an angle between the fourth center line $CL_4$ and the fifth center line $CL_5$ may be same or different.

The number of ultrasound images may be determined depending on the number of the ultrasound images to be compounded.

The processing unit 120 may be configured to set virtual common point moving positions corresponding to the center lines based on the virtual common point VP, at step S1006 in FIG. 10. The processing unit 120 may be configured to move the virtual common point VP to the virtual common point moving positions to set sub-virtual common points corresponding to the ultrasound images, at step S1008 in FIG. 10.

In one embodiment, the processing unit 120 may be configured to set a first virtual common point moving position for moving the virtual common point VP along the first center line $CL_1$. The processing unit 120 may be further configured to move the virtual common point VP to the first virtual common point moving position to set a first sub-virtual common point $SVP_1$ corresponding to the first ultrasound image $SF_1$ as shown in FIG. 11. The processing unit 120 may be also configured to set a second virtual common point moving position for moving the virtual common point VP along the second center line $CL_2$. The processing unit 120 may be further configured to move the virtual common point VP to the second virtual common point moving position to set a second virtual common point $SVP_2$ corresponding to the second ultrasound image $SF_2$ as shown in FIG. 11. The processing unit 120 may be additionally configured to set a third virtual common point moving position for moving the virtual common point VP along the third center line $CL_3$. The processing unit 120 may be further configured to move the virtual common point VP to the third virtual common point moving position to set a third sub-virtual common point $SVP_3$ corresponding to the third ultrasound image $SF_3$ as shown in FIG. 11. The processing unit 120 may be further configured to set a fourth virtual common point moving position for moving the virtual common point VP along the fourth center line $CL_4$. The processing unit 120 may be configured to move the virtual common point VP to the fourth virtual common point moving position to set a fourth sub-virtual common point $SVP_4$ corresponding to the fourth ultrasound image $SF_4$ as shown in FIG. 11. The processing unit 120 may be further configured to set a fifth virtual common point moving position for moving the virtual common point VP along the fifth center line $CL_5$. The processing unit 120 may be also configured to move the virtual common point VP to the fifth virtual common point moving position to set a fifth sub-virtual common point $SVP_5$ corresponding to the fifth ultrasound image $SF_5$ as shown in FIG. 11.

The processing unit 120 may be configured to set a plurality of scan-lines corresponding to each of the ultrasound images based on the virtual common point, the sub-virtual common points and the center lines, at step S1010 in FIG. 10.

Thus, the ultrasound data acquisition unit 110 may be configured to transmit the ultrasound signals to the living body along the scan-lines and receive the ultrasound echo signals from the living body to acquire the ultrasound data corresponding to each of the ultrasound images.

The methods of setting the plurality of scan-lines in the embodiment are similar to the methods of setting the plurality of scan-lines in the first embodiment. Thus, they have not been described in detail so as not to unnecessarily obscure the present disclosure.

The processing unit 120 may be configured to form the ultrasound images based on the ultrasound data provided from the ultrasound data acquisition unit 110, at step S1012 in FIG. 10.

In one embodiment, the processing unit 120 may be configured to form the first ultrasound image $SF_1$ based on the first ultrasound data provided from the ultrasound data acquisition unit 110, as shown in FIG. 11. The processing unit 120 may be further configured to form the second ultrasound image $SF_2$ based on the second ultrasound data provided from the ultrasound data acquisition unit 110, as shown in FIG. 11. The processing unit 120 may be also configured to form the third ultrasound image $SF_3$ based on the third ultrasound data provided from the ultrasound data acquisition unit 110, as shown in FIG. 11. The processing unit 120 may be further configured to form the fourth ultrasound image $SF_4$ based on the fourth ultrasound data provided from the ultrasound data acquisition unit 110, as shown in FIG. 11. The processing unit 120 may be further configured to form the fifth ultrasound image SF5 based on the fifth ultrasound data provided from the ultrasound data acquisition unit 110, as shown in FIG. 11.

The processing unit 120 may be configured to perform spatial compounding upon the ultrasound images to form an ultrasound spatial compound image, at step S1014 in FIG. 10. The methods of performing the spatial compounding are well known in the art. Thus, they have not been described in detail so as not to unnecessarily obscure the present disclosure. For example, the processing unit 120 may perform the spatial compounding by calculating a mean brightness value corresponding to each of the pixels of the ultrasound images.

In another embodiment, the present invention may provide a computer readable medium comprising computer executable instructions configured to perform the following acts: a) setting a plurality of center lines based on a virtual common point corresponding to predetermined scan-lines; b) moving the virtual common point along each of the center lines to set a plurality of scan-lines; c) acquiring ultrasound data by transmitting and receiving ultrasound signals based on the plurality of scan-lines; d) forming a plurality of ultrasound images corresponding to the center lines based on the ultrasound data; and e) performing spatial compounding upon the ultrasound images to form an ultrasound spatial compound image. The computer readable medium may comprise a floppy disk, a hard disk, a memory, a compact disk, a digital video disk, etc.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   an ultrasound data acquisition unit including an ultrasound probe having a curved shape, configured to acquire ultrasound data by transmitting and receiving ultrasound signals; and
   a processing unit in communication with the ultrasound data acquisition unit, the processing unit being configured to:
   set a virtual common point at which a plurality of scan-lines intersect in consideration of positions of a plurality of transducer elements in the ultrasound probe having a curved shape,
   set a plurality of center lines, each of which intersects with the ultrasound probe, converging into the virtual common point including a first center line and a second center line, the first center line passing through a first transducer element from among the plurality of transducer elements and the second center line passing through a second transducer element, different from the first transducer element, from among the plurality of transducer elements,
   set a first sub-virtual common point on the first center line apart from the virtual common point and a second sub-virtual common point on the second center line apart from the virtual common point,
   set a first plurality of scan-lines corresponding to the first center line and converging to the first sub-virtual common point to form a first ultrasound image, the first plurality of scan-lines passing through only transducer elements located in a first portion of the ultrasound probe,
   set a second plurality of scan-lines corresponding to the second center line and converging to the second sub-virtual common point to form a second ultrasound image, the second plurality of scan-lines passing through only transducer elements located in a second portion of the ultrasound probe, different from the first portion of the ultrasound probe, and
   perform spatial compounding upon a plurality of ultrasound images including the first ultrasound image and the second ultrasound image to form an ultrasound spatial compound image,
   wherein a number of the plurality of center lines is determined depending on a number of the plurality of ultrasound images to be compounded.

2. The ultrasound system of claim 1, wherein the processing unit is further configured to:
   detect a transducer element of the ultrasound probe, through which the second center line passes;
   detect a center point of the detected transducer element;
   set a reference scan-line passing through the center point of the detected transducer element on a basis of the second sub-virtual common point corresponding to the second ultrasound image;
   set the second plurality of scan-lines based on the reference scan-line and the second sub-virtual common point; and
   rotate the second center line to a third center line to set a third plurality of scan-lines.

3. The ultrasound system of claim 2, wherein the reference scan-line is a firstly scanned scan-line or a lastly scanned scan-line for the second ultrasound image.

4. The ultrasound system of claim 1, wherein the processing unit is configured to:
   detect a transducer element of the ultrasound probe, through which the first center line passes;
   detect a center point of the detected transducer element;

set a reference scan-line passing through the center point on a basis of the first sub-virtual common point corresponding to a reference ultrasound image;

set the first plurality of scan-lines based on the reference scan-line and the first sub-virtual common point; and rotate the first center line to a third center line to set a third plurality of scan-lines.

5. The ultrasound system of claim 4, wherein the reference scan-line is a firstly scanned scan-line or a lastly scanned scan-line for the reference ultrasound image.

6. The ultrasound system of claim 1, wherein the processing unit is further configured to:

set a rotating angle for rotating the second center line corresponding to the second ultrasound image based on the second sub-virtual common point;

rotate the second center line corresponding to the second ultrasound image to the rotating angle based on the second sub-virtual common point; and reset the second plurality of scan-lines based on the rotating angle.

7. A method of providing an ultrasound spatial compound image, comprising:

a) setting a virtual common point at which a plurality of scan-lines intersect in consideration of positions of a plurality of transducer elements in an ultrasound probe having a curved shape, and setting a plurality of center lines, each of which intersects with the ultrasound probe, converging into the virtual common point including a first center line and a second center line, the first center line passing through a first transducer element from among the plurality of transducer elements and the second center line passing through a second transducer element, different from the first transducer element, from among the plurality of transducer elements;

b) setting a first sub-virtual common point on the first center line apart from the virtual common point and a second sub-virtual common point on the second center line apart from the virtual common point;

c) setting a first plurality of scan-lines corresponding to the first center line and converging to the first sub-virtual common point to form a first ultrasound image, the first plurality of scan-lines passing through only transducer elements located in a first portion of the ultrasound probe;

d) setting a second plurality of scan-lines corresponding to the second center line and converging to the second sub-virtual common point to form a second ultrasound image, the second plurality of scan-lines passing through only transducer elements located in a second portion of the ultrasound probe, different from the first portion of the ultrasound probe;

e) acquiring ultrasound data by transmitting and receiving ultrasound signals based on the first and second plurality of scan-lines and forming the first ultrasound image and the second ultrasound image; and f) performing spatial compounding upon a plurality of ultrasound images including the first ultrasound image and the second ultrasound image to form an ultrasound spatial compound image, wherein a number of the plurality of center lines is determined depending on a number of the plurality of ultrasound images to be compounded.

8. The method of claim 7, wherein the step d) comprises:

detecting a transducer element of the ultrasound probe, through which the second center line passes;

detecting a center point of the detected transducer element;

setting a reference scan-line passing through the center point of the detected transducer element on a basis of the second sub-virtual common point corresponding to the second ultrasound image; and setting the second plurality of scan-lines based on the reference scan-line and second sub-virtual common point; and rotating the second center line to a third center line to set a third plurality of scan-lines.

9. The method of claim 8, wherein the reference scan-line is a firstly scanned scan-line or a lastly scanned scan-line for the second ultrasound image.

10. The method of claim 7, wherein the step c comprises:

detecting a transducer element of the ultrasound probe, through which the first center line passes;

detecting a center point of the detected transducer element;

setting a reference scan-line passing through the center point on a basis of the first sub-virtual common point corresponding to a reference ultrasound image;

setting the first plurality of scan-lines based on the reference scan-line and the first sub-virtual common point; and rotating the first center line to a third center line to set a third plurality of scan-lines.

11. The method of claim 10, wherein the reference scan-line is a firstly scanned scan-line or a lastly scanned scan-line for the reference ultrasound image.

12. The method of claim 7, wherein the step d) further comprises:

setting a rotating angle for rotating the second center line corresponding to the second ultrasound image based on the second sub-virtual common point;

rotating the second center line corresponding to the second ultrasound image to the rotating angle based on the second sub-virtual common point; and resetting the second plurality of scan-lines based on the rotating angle.

13. A non-transitory computer readable medium comprising computer executable instructions configured to perform the method of claim 7.

* * * * *